United States Patent [19]

Onodera et al.

[11] Patent Number: 4,700,012

[45] Date of Patent: Oct. 13, 1987

[54] PROCESS FOR ISOMERIZING XYLENE

[75] Inventors: Tamio Onodera; Akio Namatame; Kimihiko Sato; Koji Sumitani, all of Matsuyama, Japan

[73] Assignee: Teijin Petrochemical Industries, Ltd., Tokyo, Japan

[21] Appl. No.: 948,062

[22] Filed: Dec. 30, 1986

[51] Int. Cl.$^4$ .............................................. C07C 5/27
[52] U.S. Cl. .................................... 585/481; 585/482
[58] Field of Search .................... 585/481, 480, 482

[56] References Cited

U.S. PATENT DOCUMENTS

| | | | |
|---|---|---|---|
| 4,351,979 | 9/1982 | Chester et al. | 585/481 |
| 4,385,195 | 5/1983 | Butter et al. | 585/481 |
| 4,492,773 | 11/1984 | Chu et al. | 585/481 |
| 4,626,609 | 12/1986 | Shihabi | 585/481 |

FOREIGN PATENT DOCUMENTS

| | | | |
|---|---|---|---|
| 1195700 | 10/1985 | Canada | 585/481 |
| 0000812 | 7/1977 | European Pat. Off. | 585/481 |
| 0087906 | 2/1982 | European Pat. Off. | 585/481 |

Primary Examiner—Asok Pal
Attorney, Agent, or Firm—Wenderoth, Lind & Ponack

[57] ABSTRACT

A process for continuously isomerizing xylene, which comprises subjecting a hydrocarbon feed material comprising a major proportion of a xylene isomer mixture and a minor proportion of non-aromatic hydrocarbons to xylene isomerization reaction, isolating a specific xylene isomer from the resulting isomerization reaction mixture, and recycling the remaining hydrocarbon mixture to the xylene isomerization reaction; wherein the hydrocarbon feed material or the xylene isomerization reaction mixture is treated with hydrogen in the presence of a cracking catalyst comprising (a) a zeolite selected from zeolites ZSM-5, ZSM-11, ZSM-12, ZSM-34 and ZSM-48 series, at least 20% of its cation site being occupied by a cation of a metal selected from alkali metals and alkaline earth metals, and (b) a refractory amorphous inorganic oxide having platinum supported thereon, at a temperature and a weight hourly space velocity which simultaneously satisfy the following inequalities (i) to (iv)

$$300 \leq T \leq 425 \quad \text{(i)}$$

$$5 \leq V \leq 200 \quad \text{(ii)}$$

$$\left(\frac{4}{V} + 0.10\right) T - \frac{1000}{V} - 40 \geq 5 \quad \text{(iii)}$$

$$1.5T - 3V \leq 600 \quad \text{(iv)}$$

wherein T represents the temperature (°C.), and V represents the weight hourly space velocity (hr$^{-1}$), thereby to crack the non-aromatic hydrocarbons in the hydrocarbon feed material or the xylene isomerization reaction mixture.

9 Claims, No Drawings

PROCESS FOR ISOMERIZING XYLENE

This invention relates to an improvement in a process for isomerizing xylene. More specifically, this invention relates to an industrially advantageous process for continuously isomerizing xylene which comprises subjecting a hydrocarbon feed material comprising a major proportion of a xylene isomer mixture and a minor proportion of non-aromatic hydrocarbons to xylene isomerization reaction, isolating a specific xylene isomer, preferably p-xylene, from the resulting isomerization reaction mixture, and recycling the remaining hydrocarbon mixture to the xylene isomerization reaction; characterized in that the non-aromatic hydrocarbons, which are accumulated in the process and can reduce the efficiency of the isomerization reaction, are efficiently cracked and removed from the process while suppressing a loss of the xylenes, whereby the isomerization of xylene can be carried out continuously over a long period of time in spite of using the hydrocarbon feed material containing non-aromatic hydrocarbons.

The demand for xylenes, particularly p-xylene, has increased in proportion to an increase in the demand for polyester fibers and films. A typical process for producing p-xylene comprises a step of separating p-xylene from a $C_8$ aromatic hydrocarbon mixture as a starting material by a crystallization method or an adsorption method, a step of contacting the remainder of the hydrocarbon mixture with a catalyst for isomerizing xylenes to convert the xylenes in the remainder of the hydrocarbon mixture to a xylene isomer mixture having a composition nearly close to its thermodynamic composition, and a step of recycling the isomer mixture to the p-xylene separating step.

In the above process for producing p-xylene, it is required, for example, to make the composition of the xylene isomer mixture in the isomerization reaction product approach its thermodynamically equilibrated composition as much as possible, to suppress sidereactions involving a loss of xylenes such as disproportionation and hydrogenaration, and to convert ethylbenzene, which is difficult to separate by an ordinary distillation operation because of its boiling point being close to that of xylenes, into a lower- or heavierboiling component which is easy to separate by distillation. To meet these requirements is very important industrially in increasing the efficiency of the isomerization reaction and reducing the cost of production in the p-xylene manufacturing process. The $C_8$ aromatic hydrocarbon mixture used heretofore as a starting material in industrial practice is obtained by extracting aromatic hydrocarbons from a starting oil such as a reformed gasoline and a cracked gasoline by a method such as the arosolvan, udex or sulfolane method in order to remove non-aromatic hydrocarbons which adversely affect the efficiency of the isomerization reaction and by distilling the extract to separate each component of the aromatic hydrocarbons. The $C_8$ aromatic hydrocarbons produced by above process is a mixture typically consisting of 5 to 20% of ethylbenzene, 15 to 25% of p-xylene, 30 to 60% of m-xylene and 15–25% by weight of o-xylene. Since the above method of producing the $C_8$ aromatic hydrocarbon mixture includes the solvent extraction step, it has the defect that the equipment required becomes complex and the price of the resulting hydrocarbon mixture increases.

On the other hand, attempts have been made in recent years to increase the recovery of aromatic hydrocarbons such as benzene, toluene and xylenes in the reforming of petroleum naphtha. Particularly, as a result of improvement on catalysts which catalyze the dehydrogenating cyclization of paraffinic hydrocarbons, it has become possible to carry out the dehydrogenating cyclization under low pressures and relatively mild conditions and to get an aromatic hydrocarbon mixture having a low content of non-aromatic hydrocarbons.

With the foregoing technical background, a method was proposed for producing a $C_8$ aromatic hydrocarbon mixture having a low content of non-aromatic hydrocarbons and capable of being used for production of xylene, which comprises subjecting reformed naphtha to distillation alone without using the aforesaid solvent extraction step (Japanese Patent Publication No. 47231/1982). A method was also proposed which comprises distilling reformed naphtha, polymerizing olefins therein which are difficult to remove by distillation alone and become a poison on the xylene isomerization reaction catalyst, and again distilling the reformed oil thereby to produce a $C_8$ aromatic hydrocarbon mixture having a low content of non-aromatic hydrocarbons (Japanese LaidOpen Patent Publication No. 181036/1985). The amount of the non-aromatic hydrocarbons in the $C_8$ aromatic hydrocarbon mixture obtained by such a method is usually 0.05 to 3% by weight, typically 0.1 to 2% by weight. The non-aromatic hydrocarbons usually consist of 70 to 80% by weight of $C_{8-C10}$ paraffins and 20 to 30% by weight of $C_{8-C10}$ naphthenes.

If such a $C_8$ aromatic hydrocarbon mixture produced without going through the solvent extraction can be directly submitted to xylene isomerization reaction, the cost of the raw materials can be reduced, and consequently, it is possible to offer p-xylene at a lower price.

Although the content of the non-aromatic hydrocarbons is the $C_8$ aromatic hydrocarbon mixture is low, when it is used recyclically for a certain period of time in the production of p-xylene by xylene isomerization using this hydrocarbon mixture, the non-aromatic hydrocarbons are gradually accumulated in the process and will adversely affect the isomerization reaction of xylenes. Accordingly, it is necessary to stop the reaction regularly and replace all the hydrocarbons in the process by fresh hydrocarbons.

Thus, in spite of the fact that processes for producing a $C_8$ aromatic hydrocarbon mixture having a low content of non-aromatic hydrocarbon fractions have previously been proposed as stated above, there has been scarcely any practical process for production of p-xylene using such a $C_8$ aromatic hydrocarbon mixture as a starting material. Only U.S. Pat. No. 4,163,028 and Europe Pat. No. 102716 may be cited as prior art pertaining to such a process. Manufacturers already having a process for isomerizating xylene, however, must take the trouble of changing the catalyst and the operating conditions when they adopt the processes proposed in the prior art. Furthermore, since according to these processes, xylenes containing non-aromatic hydrocarbons are fed to a catalyst under very severe conditions, the catalytic activity is reduced with time. The activity of the catalyst to decompose the non-aromatic components is also reduced so that these components are accumulated within the recycle process and the efficiency of producing p-xylene is likely to decrease. Moreover, the above prior art references merely show the practical ability of the catalyst to decompose n-paraffin or branched monoalkylparaffins which are non-aromatic components susceptible to decomposition reaction, and do not at all teach the effectiveness of the processes on a non-aromatic hydrocarboncontaining xylene material containing naphthenes or polyalkyl-substituted paraffins.

The present inventors have made extensive investigations on a process for efficiently producing xylene isomers, particularly p-xylene, by using as a relatively cheap raw material a $C_8$ aromatic hydrocarbon mixture still containing small amounts of non-aromatic hydrocarbons without greatly changing the conventional xylene isomerization process. These investigations have now led to the present invention.

According to this invention, there is provided a process for continuously isomerizing xylene, which comprises subjecting a hydrocarbon feed material comprising a major proportion of a xylene isomer mixture and a minor proportion of non-aromatic hydrocarbons to xylene isomerization reaction, isolating a specific xylene isomer from the resulting isomerization reaction mixture, and recycling the remaining hydrocarbon mixture to the xylene isomerization reaction; wherein the hydrocarbon feed material or the xylene isomerization reaction mixture is treated with hydrogen in the presence of a cracking catalyst comprising (a) a zeolite selected from zeolites ZSM-5, ZSM-11, ZSM-12, ZSM-34 and ZSM-48 series, at least 20% of its cation site being occupied by a cation of a metal selected from alkali metals and alkaline earth metals, and (b) a refractory amorphous inorganic oxide having platinum supported thereon, at a temperature and a weight hourly space velocity which simultaneously satisfy the following inequalities (i) to (iv)

$$300 \leq T \leq 425 \quad \text{(i)}$$

$$5 \leq V \leq 200 \quad \text{(ii)}$$

$$\left(\frac{4}{V} + 0.10\right) T - \frac{1000}{V} - 40 \geq 5 \quad \text{(iii)}$$

$$1.5T - 3V \leq 600 \quad \text{(iv)}$$

wherein T represents the temperature (°C.), and V represents the weight hourly space velocity ($hr^{-1}$), thereby to crack the non-aromatic hydrocarbons in the hydrocarbon feed material or the xylene isomerization reaction mixture.

One characteristic feature of this invention is a relatively cheap hydrocarbon mixture composed mainly of a xylene isomeric mixture still containing non-aromatic hydrocarbons can be used as a feed material for xylene isomerization reaction.

The hydrocarbon feed material used in the process of this invention is composed mainly of a xylene isomer mixture and contains a small amount, generally 0.02 to 5%, preferably 0.05 to 3%, more preferably 0.1 to 1%, based on the weight of the hydrocarbon feed material, of non-aromatic hydrocarbons. The hydrocarbon feed material is produced by extracting aromatic hydrocarbons from suitable materials such as reformed or cracked gasoline using any solvent, or by a catalytic reforming process in which part of the extracting step is omitted by improving the catalyst or the operating conditions [see Oil & Gas Journal, Apr. 5, 1982, pages 210–214; Hydrocarbon Processing, Nov. 1982, pages 102–108, Hydrocarbon Processing, Nov. 1970, pages 127–136, Bull. Japan Petro. Inst., 16, 38–42 (1974)].

The composition of the hydrocarbon feed material varies depending upon the composition of the starting material or the method of production, and cannot be strictly defined. The non-aromatic hydrocarbons are paraffins and naphthenes having 8 to 10 carbon atoms and a boiling range of 120° to 150° C. Typical examples of these are linear paraffins such as octane, nonane and decane, monoalkylparaffins such as methylheptane, methyloctane, methylnonane, ethylhexane, ethylheptane and ethyloctane, dialkylparaffins such as diethylhexane, dimethylheptane, dimethyloctane, methylethylpentane, methylethylhexane and methylethylheptane, trialkylparaffins such as trimethylhexane, trimethylheptane and dimethylethylpentane, and naphthenes such as trimethylcyclohexanes and ethylmethylcyclohexanes.

The aromatic hydrocarbons in the feed material can be composed substantially only of xylene isomer mixture, but may contain up to 40%, particularly up to 20%, based on the weight of the feed material, of ethylbenzene. Rarely, the aromatic hydrocarbons contain a very small amount, usually not more than 0.1% by weight, based on the hydrocarbon feed material, of $C_9$ aromatic hydrocarbons such as cumene, ethyltoluenes and trimethylbenzenes. The presence of such very small amounts of $C_9$ aromatic hydrocarbons does not affect the practice of the process of this invention, and a hydrocarbon mixture containing such amounts of $C_9$ aromatic hydrocarbons may also be used as the feed material in the process of this invention.

Another characteristic feature of the present invention is that non-aromatic hydrocarbons contained in the hydrocarbon feed material or the xylene isomerization reaction mixture are cracked by treating the aforesaid hydrocarbon feed material or the isomerization reaction mixture obtained by subjecting the hydrocarbon feed material to xylene isomerization reaction, in the presence of a cracking catalyst composed of the specific zeolite and the refractory amorphous inorganic oxide having platinum supported thereon and at a temperature and weight hourly space velocity (to be abbreviated as "WHSV") which simultaneously satisfy the aforesaid inequalities (i) to (iv).

The cracking catalyst used in this invention is composed of the specific zeolite and the refractory inorganic oxide having platinum supported thereon.

The zeolite used in the catalyst in accordance with this invention is a zeolite selected from zeolites of the following series (literature references disclosing the composition and properties of the zeolites, the manufacturing processes, etc. are indicated in the parentheses).

Zeolite ZSM-5 (U.S. Pat. No. 3,702,886)
Zeolite ZSM-11 (U.S. Pat. No. 3,709,979)
Zeolite ZSM-12 (U.S. Pat. No. 3,832,449)
Zeolite ZSM-34 (U.S. Pat. No. 4,086,184)
Zeolite ZSM-48 (U.S. Pat. No. 4,423,021)

At least 20%, preferably 20 to 95%, more preferably 30 to 80%, of the cation site of the zeolite is occupied by a cation of at least one metal selected from alkali metals and alkaline earth metals. Examples of the metal cations are lithium, sodium, potassium, rubidium, cesium, beryllium, magnesium, calcium, strontium and barium cations. Of these, lithium, sodium and strontium cations are preferred. At least one may be present on the cation site of the zeolite, or two or more cations may be present together. By using the zeolite in which at least 20% of its cation site the acid active site based on alumina (ALO$_2^-$which is a constituent component of the zeolite]is occupied by the aforesaid alkali metal cations and/or alkaline earth metal cations, the non-aromatic hydrocarbons can be selectively cracked in a high conversion while a loss of xylenes in the hydrocarbon feed material or the xylene isomerization reaction mixture owing to disproportionation of the xylenes, etc. is suppressed. Usually proton can exist in cation sites of the zeolite which are not occupied by the alkali metal and/or alkaline earth metal cations. If desired, such cation sites may be occupied by cation of metals other than the alkali metal and alkaline earth metals, such as iron, cobalt, nickel, copper, zinc, lanthanum and cerium.

The zeolite in which at least 20% of its cation sites are occupied by the alkali metal and/or alkaline earth metal cations may be obtained by subjecting a zeolite produced as described in the above-cited literature references to ion-exchange treatment using the alkali metal and/or alkaline earth metal cations in accordance with a method known per se [for example, by J. Cat. 46, 100–108 (1977), and J. Cat., 43, 292–303 (1976)].

Regarding platinum-supported refractory inorganic oxide used in combination with the zeolite, there is no particular limitation on the refractory oxide as carrier and any conventional catalyst carriers may be equally used. Examples include silica, alumina, silicaalumina, kaolin, silica-magnesia, zeolite, zirconia and magnesia. Gamma-alumina is preferred in views of its high specific surface area.

Desirably, the amount of platinum supported on the carrier is geneally 0.005 to 5% by weight, preferably 0.001 to 3% by weight, more preferably 0.05 to 1% by weight, based on the weight of the carrier, in order to suppress hydrogenating of aromatic-ring or cracking of xylenes in the hydrocarbon feed material or the xylene isomerization reaction mixture and accelerate cracking of the non-aromatic hydrocarbons.

The platinum-supported refractory inorganic oxide may be prepared by a method known per se (see, for example, J. Mol. Cat., 25, 119–130 (1984), and Fuel Proc. Tech., 6, 177–182 (1982)]. For example, it may be prepared by impregnating a refractory inorganic oxide with an aqueous solution of a water-soluble platinum compound such as chloroplatinic acid or a platinum-tetrammine complex, removing the solvent, drying the impregnated inorganic oxide, calcining it in an air stream, and subjecting it to reduction in a reducing atmosphere.

The cracking catalyst used in this invention may be prepared by combining the zeolite and platinum-supported refractory inorganic oxide described hereinabove. The non-aromatic hydrocarbons contained in the hydrocarbon feed material submitted to the process of this invention do not undergo substantial cracking in the presence of the zeolite alone. The platinum-supported inorganic oxide alone neither shows industrially sufficient cracking activity on the non-aromatic hydrocarbons. A catalyst obtained by combining zeolite containing platinum with a refractory inorganic oxide exhibits only very low cracking activity on the non-aromatic hydrocarbons. The cracking catalyst used in the process of this invention has very high cracking activity on the non-aromatic hydrocarbons and very low disproportionating activity on xylenes as a result of the combination of the zeolite containing a specific cation and the platinumsupported refractory inorganic oxide, which leads to a synergistic effect.

The mixing ratio of the platinum-supported refractory inorganic oxide to the zeolite may be varied widely depending upon the type of the zeolite, the amount of platinum supported, etc. Generally, the weight ratio of the platinum-supported inorganic oxide to the zeolite is conveniently from 0.05 to 5, preferably from 0.1 to 3, more preferably from 0.5 to 2.

The cracking catalyst can be produced by uniformly mixing the zeolite particles of a suitable particle diameter with the platinum-supported refractory inorganic oxide particles in the aforesaid ratio, and molding the mixture into extrudates, pellets, tablets, or another catalyst shape.

According to the process of this invention, the hydrocarbon feed material or the xylene isomerization reaction mixture is contacted with the aforesaid cracking catalyst composition in the presence of hydrogen in the vapor phase to crack the non-aromatic hydrocarbons in the feed material or the reaction mixture to lower-boiling hydrocarbons. The temperature and WHSV at the time of this contacting are of important significance. In order to maximize the efficiency of cracking the non-aromatic hydrocarbons while suppressing a loss of xylenes, it has been found to be very important to select the temperature (T°C.) and WHSV (V hr$^{-1}$) such that they simultaneously satisfy the following inequalities (i) to (iv).

$$300 \leq T \leq 425 \quad \text{(i)}$$

$$5 \leq V \leq 200 \quad \text{(ii)}$$

$$\left(\frac{4}{V} + 0.10\right) T - \frac{1000}{V} - 40 \geq 5 \quad \text{(iii)}$$

$$1.5T - 3V \leq 600 \quad \text{(iv)}$$

If the temperature or WHSV does not satisfy any one of these inequalities (i) to (iv), there arise disadvantages such as the increased loss of xylenes and/or the reduced efficiency of cracking the non-aromatic hydrocarbons. For example, if the temperature (T) is lower than 300° C., the efficiency of cracking the nonaromatic hydrocarbons is very low. If it is higher than 425° C., the loss of xylenes increases. If WHSV is higher than 200, the cracking efficiency is reduced. It has further been found that when the temperature (T) and WHSV (v) satisfy inequalities (i) and (ii) but do not satisfy inequalities (iii) and (iv), the loss of xylene increases and/or the cracking efficiency is reduced.

To perform the process of this invention more efficiently, the temperature (T) and WHSV (V) should desirably be selected such that they simultaneously satisfy the following inequalities $$320 \leq T \leq 410 \quad \text{(i)}$$

$$10 \leq V \leq 100 \quad \text{(ii)}$$

$$\left(\frac{4}{V} + 0.10\right) T - \frac{1000}{V} - 40 \geq 10 \quad \text{(iii)}$$

$$1.5T - 3V \leq 570 \quad \text{(iv)}$$

and preferably the following inequalities $$350 \leq T \leq 400 \quad \text{(i)}$$
$$20 \leq V \leq 80 \quad \text{(ii)}$$
$$\left(\frac{4}{V} + 0.10\right) T - \frac{1000}{V} - 40 \geq 15 \quad \text{(iii)}$$
$$1.5T - 3V \leq 530 \quad \text{(iv)}$$

The partial pressure of hydrogen is not strictly limited, and can be varied depending upon the temperature or WHSV used, etc. Generally, it is conveniently selected from the range of generally 0.1 to 25 kg/cm$^2$, preferably 0.5 to 20 kg/cm$^2$ and more preferably 0.8 to 15 kg/cm$^2$.

The aforesaid treatment of cracking the nonaromatic hydrocarbons may be performed on the hydrocarbon feed material to be submitted to xylene isomerization reaction, or on the isomerization reaction mixture obtained by the xylene isomerization reaction and from which a specific xylene isomer, such as p-xylene, is isolated later. A specific metnod of achieving it is, for example, to provide the cracking reactor filled with the aforesaid cracking catalyst for cracking non-aromatic hydrocarbons in series forwardly or rearwardly the reactor for isomerizing xylenes, and to operate the reactor at the specified temperature and WHSV specified hereinabove.

In the process of this invention, the isomerization of xylenes may be carried out by methods known per se. For example, the following methods may be cited.

(1) A method which comprises contacting an aromatic compound mixture containing ethylbenzene and xylenes with a catalyst including ZSM-5, ZSM-12 or ZSM-21 in the vapor phase at a temperature of 500° to 1000° F. (U.S. Pat. Nos. 3,856,872 and 3,856,873).

(2) A method which comprises contacting a xylene-containing raw material with a catalyst composition comprising a zeolite selected from ZSM-5, ZSM-11, ZSM-12, ZSM-23, ZSM-35, ZSM-39 and ZSM-48 containing a noble metal at a temperature of 260° to 538° C. (preferably 427° to 482° C.), a pressure of 50 to 1000 psig, preferably 100 to 400 psig and a weight hourly space velocity of 1 to 50, preferably 5 to 15 (U.S. Pat. Nos. 4,312,790 and 4,385,195).

(3) A method which comprises contacting a xylene isomer mixture with a catalyst composition comprising platinum, a second metal (preferably a metal selected from the group consising of tin, barium, titanium, indium, cadmium and lead) and a zeolite selected from the group consisting of ZSM-5, ZSM-11, ZSM-12, ZSM-35 and ZSM-38 at a temperature of 250° to 450° C., a hydrogen pressure of 0 to 25 kg/cm$^2$ and a weight hourly space velocity of 1 to 500 (U.S. Pat. No. 4,331,822).

In the process of this invention, the isomerization of xylenes can be advantageously carried out by any of the above known methods.

A specific xylene isomer, such as p-xylene, may be isolated by methods known per se from the reaction mixture after the xylene isomerization. For example, a crystallization method described, for example, in Oil & Gas Journal—Sept. 15, 1975, pages 201–202 and Hydrocarbon Processing Nov. 1985, page 175, or an adsorption method described, for example, in Ind. Eng. Chem. Prod. Res. Dev., 18 (4), 263–268 (1979), and Hydrocarbon Processing, Nov., 1985, page 176 may be employed.

The hydrocarbon mixture left after isolation of the specific xylene isomer as above is mixed with a fresh feed of the hydrocarbon and may be recycled to the xylene isomerization reactor directly or via the non-aromatic hydrocarbon cracking reactor.

The process of this invention described hereinabove brings about various advantages among which are:

(a) The process does not require an operation of removing the non-aromatic hydrocarbons by the solvent extraction method which involves a complex operation and a apparatus, and permits use of a relatively cheap C$_8$ aromatic hydrocarbon mixture, which contains small amounts of non-aromatic hydrocarbons and can be obtained by a distillation operation alone, as a starting material.

(b) Even when the process is operated continuously over a long period of time, the non-aromatic hydrocarbons are not accumulated within the xylene isomerization reaction mixture, and the isomerization of xylenes can be performed with good efficiency.

The following examples illustrate the present invention more specifically.

REFERENTIAL EXAMPLE 1

Preparation of zeolites:-
(a) Zeolite ZSM-5

Zeolite ZSM-5 was synthesized in accordance with the method disclosed in U.S. Pat. No. 3,965,207. In the synthesis, water glass was used as a source of silica, and aluminum sulfate was used as a source of alumina. Tri-n-propylamine and n-propyl bromide were used as a source of organic nitrogen cation and methyl ethyl ketone was further added. The reaction was carried out under predetermined conditions in an autoclave. The product was filtered, washed fully with decationized water, and dried overnight in an electric oven at 100° C. X-ray diffraction determined the product to be ZSM-5. Chemical analysis showed that the product had a silica/alumina mole ratio of 70.

(b) Zeolite ZSM-11

Zeolite ZSM-11 was synthesized in accordance with the method disclosed in U.S. Pat. No. 3,709,979. In the synthesis, water glass was used as a source of silica; aluminum sulfate, as a source of alumina; and tetra-n-butyl ammonium bromide, as a source of organic nitrogen cation. The reaction was carried out under predetermined conditions in an autoclave. The product was filtered, washed well with decationized water, and dried overnight in an electric oven at 100° C. X-ray difraction analysis determined the product to be ZSM-11. It was found that the product had a silica/alumina mole ratio of 58.

(c) Zeolite ZSM-34

Zeolite ZSM-34 was synthesized in accordance with the method disclosed in U.S. Pat. No. 4,086,184. In the synthesis, silica sol (30wt. % SiO$_2$) was used as a source of silica; sodium aluminate, as a source of alumina; and choline, as a source of organic nitrogen cation. The reaction was carried out under predetermined conditions in an autoclave. The product was filtered, washed well with decationized water, and dried overnight at 100° C. X-ray difraction analysis determined the product to be ZSM-34. It was found that the product had a silica/alumina mole ratio of 20.

(d) Zeolite ZSM-48

Zeolite ZSM-48 was synthesized in accordance with the method disclosed in U.S. Pat. No. 4,423,021. In the synthesis, silica sol (30 wt. % SiO$_2$) was used as a source of silica; aluminum sulfate, as a source of alumina; and hexamethylenediamine, as a source of organic nitrogen cation. The reaction was carried out under predetermined conditions in an autoclave. The product was filtered, washed well with decationized water, and dried overnight at 100° C. X-ray diffraction analysis determined the product to be ZSM-48. It was found that the product had a silica/alumina mole ratio of 130.

(e) Zeolite ZSM-12

Zeolite ZSM-12 was synthesized in accordance with the method disclosed in U.S. Pat. No. 4,552,738. In the synthesis, silica sol (30wt. % $SiO_2$) was used as a source of silica; aluminum sulfate, as a source of alumina; and benzyltriethyl ammonium chloride, as an organic template. The reaction was carried out under predetermined conditions in an autoclave. The product was filtered, washed well with decationized water, and dried overnight in an electric oven at 100° C. X-ray diffraction analysis determined the product to be ZSM-12. It was found that the product had a silica/alumina mole ratio of 150.

REFERENTIAL EXAMPLE 2

Preparation of $NH_4^{30}$-form zeolites:-

The cation sites of the zeolites obtained in Referential Example 1, (a) to (e) were converted from the sodium ion to an ammonium ion. Specifically, the zeolites were each treated with 10 ml, per gram of zeolite, of a 10% aqueous solution of ammonium chloride under reflux for 16 hours. This operation was repeated twice, and the product was filtered, washed with decationized water and dried at 100° C. for 16 hours to give $NH_4^+$-form zeolites.

REFERENTIAL EXAMPLE 3

Preparation of alumina containing platinum:-

One gram of commercial chloroplatinic acid ($H_2PtCl_6 \cdot 6H_2O$, special reagent grade made by Wako Pure Chemicals, Co., Ltd.) was dissolved in 50 ml of water. 5.32 ml of the resulting solution was taken into a 200 ml eggplant-shaped flask, and diluted with 100 ml of water. Twenty grams of alumina gel (300 mesh, a product of Wako Pure Chemicals Co., Ltd.) was added to the solution in the flask. With stirring, the mixture was mainained at 50° C. for 8 hours. Then, water was evaporated under the vacuum at 40° C. by a rotary evaporator. Subsequently, the residue was dried at 100° C. for 16 hours, and then at 200° C. for 8 hours, to prepare alumina containing 0.2% platinum.

EXAMPLE 1

Preparation of non-aromatic hydrocarbon cracking catalysts used in this invention:-

(a) $LiNO_3$ (0.64 g) was dissolved in 20 ml of water, and 10 g of $NH_4^+$-ZSM-5 obtained in Referential Example 2 was added to the aqueous solution. The mixture was maintained overnight under reflux, filtered, and fully washed with decationized water. The product was dried for 16 hours in an electric oven at 100° C. Chemical analysis showed that the dried powder obtained contained 0.16wt. % of Li. Accordingly, in the resulting product, 50% of the cation sites based on alumina was occupied by Li. To the resulting Li-containing ZSM-5 was added an equal weight of alumina containing 0.2wt. % platinum prepared in Referential Example 3, and they were fully mixed. The mixture was then molded into a size of 10 to 20 mesh to form a catalyst composition (designated as catalyst A).

(b) Thirty milliliters of a 10% aqueous solution of $Sr(NO_3)_2$ was prepared, and 10 g of $NH_4^+$-ZSM-5 obtained in Referential Example 2 was added. The mixture was maintained overnight under reflux, then filtered and well washed with decationized water. This operation was further repeated once. The resulting dried powder contained 1.6wt. % of Sr, and 78% of its cation site was occupied by Sr. To the resulting Sr-containing ZSM-5 was added an equal weight of alumina containing 0.2 wt. % platinum prepared in Referential Example 3. They were well mixed, and molded to a size of 10 to 20 mesh to prepare a composition (designated as catalyst B).

(c) NaNO (1.8 g) was dissolved in 30 ml of water, and using the aqueous solution, 10 g of $MH_4^{30}$-ZSM-11 was subjected to ion exchange. The dried powder obtained after ion exchange contained 0.45wt. % of Na, and 35% of its cation site was occupied by Na. It was worked up as in (a) above to prepare a composition (designated catalyst C).

(d) $LiNO_3$ (2.12 g) was dissolved in 30 ml of water, and using the resulting solution, 10 g of $NH_4^+$-ZSM-34 was subjected to ion exchange. The dried powder obtained after the ion exchange contained 0.66wt. % of Li, and therefore, 62% of its cation site was occupied by Li. The dried powder was then worked up as in (a) above to prepare a composition (designated as catalyst D).

(e) $LiNO_3$ (2 g) was dissolved in 30 ml of water, and using the resulting solution, 10 grams of $NH_4^+$-ZSM-48 was subjected to ion exchange. The dried powder obtained after the ion exchange contained 0.14wt. % of Li, and therefore, 80% of its cation site was occupied by Li. The dried powder was then worked up as in (a) above to prepare a composition (designated as catalyst E).

(f) $LiNO_3$ (2 g) was dissolved in 30 ml of water, and using the resulting solution, 10 g of $NH_4^+$-ZSM-12 was subjected to ion exchange. The dry powder obtained after the ion exchange contained 0.11 wt. % of Li, and therefore, 70% of its cation site was occupied by Li. The dried powder was then worked up as in (a) above to prepare a composition (designated as catalyst F).

EXAMPLE 2

This example shows that the catalysts obtained by the process of this invention show high cracking activity on non-aromatic hydrocarbons.

In each run, 1.0 g of the pelletized catalysts (A) to (F) prepared in Example 1 was loaded in a flowing-type atmospheric pressure fixed bed reactor. The temperature was elevated to 400° C. in a stream of nitrogen, and at 400° C., the nitrogen stream was replaced by a stream of hydrogen, and the catalyst was maintained as such for 2 hours to reduce platinum. Then, the temperature was adjusted to 380° C. in a stream of hydrogen, and after the catalyst layer became stable at this temperature, a xylene mixture containing $C_8$ paraffins and naphthenes was fed into the reactor and reacted at a temperature of 380° C. and a weight hourly space velocity of 10 $hr^{-1}$. The hydrogen/starting hydrocarbon mixture mole ratio was 1.

The composition of the product obtained 1 to 3 hours after the feeding of the starting mixture is shown in Table 1.

When the reaction temperature and the WHSV in this example are substituted for T and V in inequalities (iii) and (iv) given in claim 10 of this application, the left terms of these inequalities became 50 and 540, respectively. This shows that the reaction temperature and WHSV in this example satisfy the inequalities (iii) and (iv).

TABLE 1

| | Material composition (wt. %) | Product composition (wt. %) | | | | | |
|---|---|---|---|---|---|---|---|
| | | CAT.-A | CAT.-B | CAT.-C | CAT.-D | CAT.-E | CAT.-F |
| Composition | | | | | | | |
| $C_7^-$ paraffins | — | 1.28 | 1.63 | 1.35 | 0.73 | 0.77 | 0.86 |
| n-octane | 0.90 | 0.50 | 0.36 | 0.47 | 0.64 | 0.59 | 0.56 |
| 3-methylpentane | 0.30 | 0.19 | 0.17 | 0.20 | 0.25 | 0.23 | 0.23 |
| 2,5-dimethylhexane | 0.30 | 0.23 | 0.15 | 0.22 | 0.26 | 0.24 | 0.24 |
| dimethylcyclohexane | 0.80 | 0.51 | 0.39 | 0.47 | 0.58 | 0.59 | 0.53 |
| iso-octane | 1.00 | 0.89 | 0.87 | 0.88 | 0.90 | 0.92 | 0.90 |
| benzene | — | 0.85 | 0.72 | 0.80 | 0.18 | 0.12 | 0.06 |
| toluene | 1.21 | 1.32 | 1.24 | 1.28 | 1.97 | 1.65 | 1.48 |
| ethylbenzene | 11.73 | 10.29 | 10.50 | 10.37 | 10.93 | 11.20 | 11.48 |
| p-xylene | 8.80 | 17.86 | 17.25 | 15.48 | 14.49 | 13.30 | 12.10 |
| m-xylene | 55.68 | 46.18 | 46.81 | 48.57 | 47.65 | 48.85 | 51.27 |
| o-xylene | 19.18 | 19.32 | 19.43 | 19.37 | 20.38 | 20.88 | 19.86 |
| $C_9^+$ aromatics | 0.10 | 0.58 | 0.48 | 0.54 | 1.04 | 0.66 | 0.43 |
| Cracking ratio (%) | | | | | | | |
| n-octane | | 44 | 60 | 53 | 29 | 35 | 38 |
| 3-methylpentane | | 37 | 44 | 35 | 16 | 23 | 24 |
| 2,5-dibutylhexane | | 23 | 30 | 27 | 13 | 19 | 21 |
| dimethylcyclohexane | | 36 | 51 | 41 | 27 | 26 | 34 |
| iso-octane | | 11 | 13 | 12 | 10 | 8 | 10 |
| Xylene loss (%) | | 0.35 | 0.20 | 0.29 | 1.35 | 0.75 | 0.50 |

$$\text{Xylene loss} = \frac{\text{Concentration of xylene in the feed} - \text{Concentration of xylene in the product}}{\text{(Concentration of xylene in the feed)}} \times 100$$

$$\text{Cracking ratio} = \frac{\text{Concentration of the compound in the feed} - \text{Concentration of the compound in the product}}{\text{(Concentration of the compound in the product)}} \times 100$$

COMPARATIVE EXAMPLE 1

This comparative example shows that when the catalyst does not contain the platinum-containing inorganic oxide as a component, the process of this invention cannot be carried out.

To each of the zeolites containing Li, Sr or Na cation prepared in Example 1, (a), (b) and (c) was added an equal weight of chromatographic alumina gel (smaller than 300 mesh), and they were fully mixed. The mixture was molded to a size of 10 to 20 mesh to prepare catalysts A-1, B-1 and C-1, respectively. The catalysts were each calcined at 450° C. for 8 hours in an electric muffle furnace. Each of the resulting catalysts (1.0 g) was loaded in a flowing-type atmospheric pressure fixed bed reactor, and without performing the operation of reducing the catalyst, its activity of cracking the nonaromatic hydrocarbons was tested by the same method and under the same conditions as in Example 2.

The results are shown in Table 2.

It is seen that the cracking activity to the non-aromatic components was very low, or the cracking reaction did not at all proceed.

TABLE 2

| | Material composition (wt. %) | Product composition (wt. %) | | |
|---|---|---|---|---|
| | | A-1 | B-1 | C-1 |
| Composition | | | | |
| $C_7^-$ paraffin | — | 0.52 | 0.55 | 0.20 |
| n-octane | 0.90 | 0.78 | 0.74 | 0.81 |
| 3-methylpentane | 0.30 | 0.28 | 0.27 | 0.29 |
| 2,5-dimethylhexane | 0.30 | 0.29 | 0.29 | 0.29 |
| dimethylcyclohexane | 0.80 | 0.73 | 0.70 | 0.75 |
| iso-octane | 1.00 | 1.00 | 1.00 | 1.00 |
| benzene | — | 0.82 | 0.70 | 0.12 |
| toluene | 1.21 | 1.38 | 1.34 | 1.67 |
| ethylbenzene | 11.73 | 10.33 | 10.54 | 11.19 |
| p-xylene | 8.80 | 18.00 | 17.42 | 15.60 |
| m-xylene | 55.68 | 45.96 | 46.54 | 46.50 |
| o-xylene | 19.18 | 19.31 | 19.39 | 20.89 |
| $C_9^+$-aromatics | 0.10 | 0.60 | 0.52 | 0.69 |
| Cracking ratio | | | | |
| n-octane | | 13 | 18 | 10 |
| 3-methylpentane | | 7 | 9 | 3 |
| 2,5-dimethylhexane | | 3 | 4 | 3 |
| dimethylcyclohexane | | 9 | 12 | 6 |
| iso-octane | | 0 | 0 | 0 |
| Xylene loss (%) | | 0.47 | 0.37 | 0.80 |

COMPARATIVE EXAMPLE 2

This comparative example shows that when the cation site of a crystalline alumino silicate zeolite which is a catalyst component for cracking the nonaromatic hydrocarbons is occupied substantially by ammonium cations or protons, the loss of xylenes is very large, and the purpose of this invention cannot be achieved.

To each of the $NH_4^+$-form ZSM-5, ZSM-11 and ZSM-48 obtained in Referential Example 2 was added an equal weight of alumina containing 0.2wt. % platinum prepared in Referential Example 3. The mixture was molded to a size of 10 to 20 mesh to prepare catalysts (A-2, C-2 and E-2, respectively). Each of the catalysts was calcined at 450° C. for 8 hours in an electrical muffle furnace, and 1.0 g of the catalyst was loaded in a flowing-type atmospheric pressure fixed bed reactor. Thereafter, the performance of the catalyst was valuated by the same method and under the same conditions as in Example 2. The composition of the product obtained 1 to 3 hours after the feeding of the starting material is shown in Table 3.

It is seen that the xylene loss was very large compared with the results in Example 2.

TABLE 3

| Composition | Material composition (wt. %) | Product composition (wt. %) | | |
|---|---|---|---|---|
| | | A-2 | C-2 | E-2 |
| $C_7^-$ paraffin | — | 1.97 | 1.99 | 0.81 |
| n-octane | 0.90 | 0.44 | 0.41 | 0.57 |
| 3-methylpentane | 0.30 | 0.17 | 0.19 | 0.23 |
| 2,5-dimethylhexane | 0.30 | 0.22 | 0.22 | 0.24 |
| dimethylcyclohexane | 0.80 | 0.49 | 0.46 | 0.58 |
| iso-octane | 1.00 | 0.88 | 0.87 | 0.92 |
| benzene | — | 2.44 | 2.33 | 0.14 |
| toluene | 1.21 | 1.51 | 1.45 | 1.90 |
| ethylbenzene | 11.73 | 7.59 | 7.77 | 11.11 |
| p-xylene | 8.80 | 19.81 | 19.68 | 16.79 |
| m-xylene | 55.68 | 44.14 | 44.30 | 46.08 |
| o-xylene | 19.18 | 18.87 | 18.94 | 19.70 |
| $C_9^+$ aromatics | 0.10 | 1.47 | 1.39 | 0.93 |
| Cracking ratio | | | | |
| n-octane | | 51 | 55 | 37 |
| 3-methylpentane | | 42 | 37 | 24 |
| 2,5-dimethhexane | | 26 | 28 | 20 |
| dimethylcyclohexane | | 39 | 43 | 27 |
| iso-octane | | 12 | 13 | 8 |
| Xylene loss (%) | | 1.00 | 0.89 | 1.30 |

REFERENTIAL EXAMPLE 4

Preparation of xylene isomerization catalysts:-

(a) Pt-Sn-ZSM5 was prepared in accordance with the preparation of catalyst No. A-2 described in Table 1, Example 1 of U.S. Pat. No. 4,331,822.

Fifty milligrams of $[Pt(NH_3)_4]Cl_2 \cdot H_2O$ was dissolved in 30 ml of water, and 10 g of $NH_4^+$-ZSM-5 obtained in Referential Example 2 above was added to the solution. The mixture was stirred at 50° C. for 6 hours, and the product was filtered, fully washed with decationized water, then dried in an electrical oven at 100° C. for 8 hours and then at 200° C. for 16 hours, and further calcined at 450°0 C. for 8 hours in an electrical muffle furnace in a stream of air to give Pt-ZSM-5. $SnCl_2 \cdot 2H_2O$ (114 mg) was dissolved in 1 ml of conc. hydrochloric acid and 99 ml of water. Ten milliliters of the solution was taken, and 20 ml of water was added. Then, 10 g of PT-ZSM-5 was suspended in the solution and stirred at 50° C. for 5 hours. Water was evaporated at 40° C. using a rotary evaporator. Then, the residue as dried at 100° C. for 8 hours, and further calcined at 450° C. for 8 hours in an electrical muffle furnace in an atmosphere of air. The resulting Pt-Sn-ZSM-5 was mixed with chromatographic alumina gel (300 mesh) in a weight ratio of 1:1, and molded into a size of 10 to 20 mesh. The resulting catalyst is designated as CAT-X.

(b) High-silica platinum-containing ZSM-5 was prepared in accordance with Example 6 of Japanese Laid-open Patent Publication No. 24834/1984. The product obtained was separated, washed with water, dried, and then subjected to exchange by ammonium cation using a 10% aqueous solution of $NH_4Cl$. The resulting product was dried at 100° C. for 8 hours and calcined at 500° C. for 16 hours. The resulting zeolite had a silica alumina mole ratio of 1100 and contained 0.16% by weight of platinum. The resulting high-silica Pt-ZSM-5 was mixed with chromatographic alumina gel (300 mesh) in a weight ratio of 1:1, and molded to a size of 10 to 20 mesh. The resulting catalyst is designated as CAT-Y.

(c) Ni-mordenite containing 0.3% Ni was prepared by using the $NH_4^+$ mordenite obtained in Referential Example 2. $Ni(NO_3)_2 \cdot 4H_2O$ (150 mg) was dissolved in 50 ml of water), and 10 g the $NH_4^+$-of the mordenite was suspended in the solution. The suspension was stirred at 50° C. for 5 hours, and water was evaporated at 40° C. using a rotary evaporator. The residue was dried at 100° C. for 8 hours and calcined at 450° C. for 8 hours in an air atmosphere in an electrical muffle furnace. The resulting Ni-containing mordenite was mixed with chromatographic alumina gel (300 mesh) in a weight ratio of 1:1, and the mixture was molded to a size of 10 to 20 mesh. The resulting catalyst is designated as CAT-Z.

EXAMPLE 3

This example shows that the process of this invention makes it possible to crack non-aromatic hydrocarbon components efficiently under mild conditions in the treatment of a xylene mixture containing the nonaromatic hydrocarbons, and also to carry out xylene isomerization reaction rapidly.

(a) CAT-X (1.0 g) obtained in Referential Example 4 was calcined at 450° C. for 8 hours in an air atmosphere, and then loaded in a flowing-type atmospheric pressure fixed bed reactor. The temperature was elevated to 400° C. in a stream of nitrogen. At 400° C., the nitrogen stream was replaced by a stream of hydrogen and the catalyst was maintained as such for 2 hours to perform reduction. In a stream of hydrogen, the temperature was then lowered to 380° C., and after the catalyst layer became stable at this temperature, a xylene mixture containing non-aromatic hydrocarbons was fed into the reactor, and reacted at a reaction temperture of 380° C. and a WHSV of 10 $hr^{-1}$. The hydrogen/starting mixture mole ratio was maintained at 1. The product obtained 1 to 3 hours after the feeding of the starting mixture was analyzed. The same test as above was carried out under the reaction conditions indicated in Table 4 on CAT-Y and CAT-Z. The results are shown in Table 4.

(b) Xylene isomerization catalyst X (1.0 g) obtained in Referential Example 4 was loaded in a down-flow-type atmospheric pressure fixed bed reactor (catalyst layer II), and then 0.5 g of catalyst A obtained in Example 1 for cracking non-aromatic hydrocarbons was loaded in it (catalyst layer I). After the catalysts were pre-treated as in (a) above, a xylene mixture containing non-aroamtic hydrocarbons was fed into the reactor.

By the same method as above, any one of the catalysts X, Y and Z prepared in Referential Example 4 was combined with any one of the catalysts A to F prepared in Example 1, and a xylene mixture containing non-aromatic hydrocarbons was isomerized. The reaction conditions and the results of analysis of the product obtained 1 to 3 hours after the feeding of the starting mixture are summarized in Table 4. The temperatures and WHSV values in the reaction conditions satisfied the inequalities given in claim 1 of this application.

The results demonstrate that the process of this invention makes it possible to perform cracking of the non-aromatic hydrocarbons and isomerization of xylenes without an increase in the undesirable side-reactions.

TABLE 4

| $^1$Catalyst layer I<br>$^2$Catalyst layer II | Material Composition (wt. %) | Product composition (wt. %) | | | | | | |
|---|---|---|---|---|---|---|---|---|
| | | — <br> X | — <br> Y | — <br> Z | A(0.5)$^5$ <br> X (1) | B(0.5) <br> X (1) | E(0.26) <br> Y (1) | F(0.13) <br> Z (1) |
| Reaction conditions | | | | | | | | |
| Temperature (°C.) | | 380 | 430 | 430 | 380 | 380 | 410 | 410 |
| $^3$WHSV-1 (hr$^{-1}$) | | — | — | — | 20 | 20 | 15 | 15 |
| $^4$WHSV-2 (hr$^{-1}$) | | 10 | 4 | 2 | 10 | 10 | 4 | 2 |
| H$_2$/HC | | 1 | 1 | 1 | 1 | 1 | 1 | 1 |
| Composition | | | | | | | | |
| C$_7^-$ paraffin | — | 0.46 | 1.04 | 0.34 | 0.98 | 1.04 | 0.94 | 0.71 |
| n-octane | 0.88 | 0.79 | 0.67 | 0.72 | 0.58 | 0.46 | 0.59 | 0.62 |
| 3-methylpentane | 0.20 | 0.19 | 0.18 | 0.19 | 0.15 | 0.13 | 0.16 | 0.18 |
| 2,5-dimethylhexane | 0.22 | 0.21 | 0.20 | 0.21 | 0.19 | 0.18 | 0.18 | 0.18 |
| dimethylcyclohexane | 0.80 | 0.75 | 0.72 | 0.74 | 0.62 | 0.55 | 0.60 | 0.65 |
| i-octane | 0.90 | 0.88 | 0.87 | 0.90 | 0.83 | 0.81 | 0.83 | 0.83 |
| benzene | — | 0.92 | 1.76 | 0.27 | 1.24 | 1.20 | 0.79 | 0.22 |
| toluene | 1.40 | 1.50 | 1.85 | 2.57 | 1.59 | 1.60 | 1.48 | 2.41 |
| ethylbenzene | 11.80 | 10.32 | 8.81 | 9.99 | 9.81 | 9.94 | 10.46 | 10.28 |
| p-xylene | 8.72 | 19.52 | 19.86 | 17.49 | 19.73 | 19.69 | 18.68 | 16.93 |
| m-xylene | 56.23 | 44.82 | 44.36 | 44.62 | 45.16 | 45.13 | 45.39 | 45.11 |
| o-xylene | 18.84 | 19.21 | 19.01 | 19.12 | 18.51 | 18.64 | 19.45 | 19.33 |
| C$_9^+$-aromatics | 0.01 | 0.44 | 0.66 | 2.84 | 0.53 | 0.60 | 0.44 | 2.63 |
| Cracking ratio (%) | | | | | | | | |
| n-octane | | 10 | 24 | 18 | 34 | 48 | 33 | 30 |
| 3-methylpentane | | 5 | 12 | 5 | 25 | 35 | 20 | 10 |
| 2,5-dimethylhexane | | 4 | 8 | 6 | 14 | 18 | 18 | 18 |
| dimethylcyclohexane | | 6 | 10 | 7 | 22 | 31 | 25 | 19 |
| i-octane | | 2 | 3 | — | 8 | 10 | 8 | 8 |
| PX approach to equilibrium (%) | | 98.2 | 102.0 | 85.5 | 100.5 | 100.0 | 91.3 | 78.8 |
| EB decomposition ratio (%) | | 12.6 | 24.7 | 15.3 | 16.8 | 15.8 | 11.3 | 12.9 |
| Xylene loss (%) | | 0.30 | 0.67 | 3.06 | 0.36 | 0.39 | 0.32 | 2.88 |

$$\text{PX approach to equilibrium} = \frac{\left(\begin{array}{c}\text{Concentration} \\ \text{of p-isomer of} \\ \text{product xylenes}\end{array}\right) - \left(\begin{array}{c}\text{Concentration} \\ \text{of p-isomer in} \\ \text{feed xylenes}\end{array}\right)}{\left(\begin{array}{c}\text{Equilibrium concentration} \\ \text{of p-isomer at the} \\ \text{reaction temperature}\end{array}\right) - \left(\begin{array}{c}\text{Concentration} \\ \text{of p-isomer in} \\ \text{feed xylenes}\end{array}\right)} \times 100$$

$$\text{EB decomposition ratio} = \frac{\left(\begin{array}{c}\text{Concentration} \\ \text{of ethylbenzene} \\ \text{in the feed}\end{array}\right) - \left(\begin{array}{c}\text{Concentration} \\ \text{of ethylbenzene} \\ \text{in the product}\end{array}\right)}{(\text{Concentration of ethylbenzene in the feed})} \times 100$$

The notes to Table 4 are as follows:
$^1$catalyst for cracking the non-aromatic hydrocarbons
$^2$catalyst for isomerizing xylenes
$^3$based on the catalyst layer I
$^4$based on the catalyst layer II
$^5$the weight ratio of catalyst layer I to catalyst layer II

EXAMPLE 4

This example shows the process of this invention carried out under the pressure.

(a) The xylene isomerization catalyst X (8 g) prepared in Referential Example 4 was loaded in a down-flow-type elevated pressure fixed bed reactor, and subjected to reduction under the conditions described in Example 3, (a). A xylene mixture containing non-aromatic hydrocarbons having the composition indicated in Table 5 was fed into the reactor.

(b) The same test as in (a) above was carried out using the xylene isomerization catalyst Y prepared in Referential Example 4.

(c) The xylene isomerization catalyst X (8 g) prepared in Referential Example 4 was loaded in a down-flow-type elevated pressure fixed bed reactor, and then 2 g of the catalyst B prepared in Example 1 for cracking non-aromatic hydrocarbons was loaded over the catalyst X. The catalysts were subjected to reduction under the conditions described in Example 3, (a). A xylene mixture containing non-aromatic hydrocarbons having the composition indicated in Table 5 was fed into the reactor.

(d) The same test as in (c) above was carried out using the xylene isomerization catalyst Y and the non-aromatic hydrocarbon cracking catalyst A.

(e) The same test as in (c) in above was carried out using the xylene isomerization catalyst X and the non-aromatic hydrocarbon cracking catalyst F.

Table 5 shows the compositions of the feed materials used in (a) to (e), the compositions of the catalysts, the reaction conditions, and the compositions of the products obtained in 46 to 54 hours after the feeding of the feed material. The temperatures and WHSV values in the reaction conditions satisfied the inequalities given in claim 1.

The results show that the process of this invention under pressure makes it possible to react the non-aromatic hydrocarbons at a high conversion without reducing the efficiency of the xylene isomerization reaction.

TABLE 5

| | Material composition (wt. %) | Product composition (wt. %) | | | | |
|---|---|---|---|---|---|---|
| Catalyst layer I | | — | — | B (0.25) | A (0.2) | C (0.25) |
| Catalyst layer II | | X | Y | X (1) | Y (1) | X (1) |
| Reaction conditions | | | | | | |
| Temperature (°C.) | | 380 | 405 | 380 | 405 | 380 |
| Pressure (psig) | | 120 | 120 | 120 | 120 | 120 |
| WHSV-1 (hr$^{-1}$) | | — | — | 40 | 50 | 40 |
| WHSV-2 (hr$^{-1}$) | | 10 | 10 | 10 | 10 | 10 |
| H$_2$/HC (mole ratio) | | 2 | 2 | 2 | 2 | 2 |
| Composition | | | | | | |
| C$_8^-$NA | — | 0.73 | 0.70 | 1.04 | 1.19 | 0.95 |
| nonane | 0.32 | 0.25 | 0.24 | 0.18 | 0.16 | 0.19 |
| methyloctanes | 0.72 | 0.62 | 0.59 | 0.51 | 0.46 | 0.52 |
| dimethylheptanes | 0.20 | 0.19 | 0.18 | 0.16 | 0.15 | 0.16 |
| trimethylcyclohexanes | 0.25 | 0.22 | 0.21 | 0.19 | 0.17 | 0.20 |
| benzene | — | 1.32 | 1.07 | 1.48 | 1.63 | 1.36 |
| toluene | 1.46 | 1.64 | 1.80 | 1.65 | 1.78 | 1.70 |
| ethylbenzene | 10.61 | 8.22 | 8.53 | 7.99 | 7.77 | 8.18 |
| p-xylene | 9.08 | 20.42 | 20.14 | 20.48 | 20.35 | 20.27 |
| m-xylene | 57.46 | 45.78 | 45.87 | 45.72 | 45.65 | 45.78 |
| o-xylene | 19.80 | 19.62 | 19.66 | 19.59 | 19.57 | 19.62 |
| C$_9^+$-aromatics | 0.09 | 1.07 | 1.06 | 1.13 | 1.20 | 1.15 |
| NA cracking ratio (%) | | | | | | |
| nonane | | 21.8 | 23.6 | 43.7 | 49.8 | 40.6 |
| methyloctanes | | 13.8 | 18.4 | 29.7 | 36.1 | 27.8 |
| dimethylheptanes | | 5.0 | 10.0 | 20.0 | 25.0 | 20.0 |
| trimethylcyclohexanes | | 12.0 | 16.0 | 24.0 | 32.0 | 20.0 |
| PX approach to equilibrium (%) | | 101.5 | 100.0 | 102.1 | 102.1 | 100.5 |
| EB decomposition ratio (%) | | 22.5 | 19.6 | 24.7 | 26.8 | 22.9 |
| Xylene loss (%) | | 0.58 | 0.78 | 0.64 | 0.89 | 0.76 |

EXAMPLE 5

This Example was carried out in order to examine the effect of the concentration of platinum in the platinum-containing refractory inorganic oxide in the catalyst for cracking the non-aromatic hydrocarbons.

Alumina containing 0.03, 0.2, 0.5 or 1.8wt. % of platinum was prepared in accordance with the method described in Referential Example 3 with varying amounts of an aqueous solution of chloroplatinic acid. Li-ZSM-5 prepared in Example 1, (a) was mixed with an equal amount of each platinum-containing alumina, and the mixture was molded to a size of 10 to 20 mesh. The molded product was calcined at 450° C. for 8 hours in an air atmosphere, and 2.5 g of the resulting catalyst was loaded in a fixed bed reactor. Thereafter, in accordance with the conditions described in Example 3, (a), the catalyst was subjected to reduction, and a xylene mixture containing non-aromatic hydrocarbons having the composition shown in Example 4 was fed, and reacted at a temperature of 380° C., a total pressure of 120 psia and a WHSV of 40 hr$^{-1}$. The mole ratio of hydrogen to the starting hydrocarbon mixture was 2. The composition of the products obtained in 46 to 54 hours after the feeding of the starting mixture is shown in Table 6.

The results show that when the concentration of platinum in alumina is low, the cracking of the nonaromatic hydrocarbons is insuffieint, and that if the platinum concentration is too high, the cracking and the hydrogenation to the aromatic hydrocarbons undesirably occur, resulting in an increase in xylene loss.

TABLE 6

| Platinum concentration in alumina (wt. %) | 0.03 | 0.2 | 0.5 | 1.8 |
|---|---|---|---|---|
| Non-aromatic component cracking ratio (%) | | | | |
| nonane | 18.4 | 39.1 | 48.2 | 52.6 |
| methyloctanes | 13.7 | 27.4 | 31.6 | 34.4 |
| dimethylheptanes | 9.3 | 18.7 | 23.9 | 26.1 |
| trimethylcyclohexanes | 11.0 | 23.0 | 28.4 | 30.9 |
| Aromatic ring loss (%) | 0.03 | 0.11 | 0.45 | 0.60 |
| Xylene loss (%) | 0.06 | 0.16 | 0.70 | 1.08 |

EXAMPLE 6

This Example was carried out in order to examine the effects of the reaction temperature and WHSV on the reaction characteristics in the treatment of a xylene mixture containing non-aromatic hydrocarbons.

The catalyst B (2.5 g) prepared in Example 1, (b) was loaded in a fixed bed reactor, and then subjected to reduction by the method described in Example 3, (a). Then, a xylene mixture containing non-aromatic hydrocarbons having the composition shown in Example 4 was fed into the reactor, and reacted under the temperature and WHSV shown in Table 7 and a total pressure of 120 psia. The hydrogen/hydrocarbon mole ratio was 2. The composition of the product obtained in 46 to 54 hours after the feeding of the starting mixture is shown in Table 7.

The results show that at the reaction temperatures and WHSV values specified in this invention, the xylene loss is suppressed, and the non-aromatic hydrocarbon are decomposed efficiently.

TABLE 7

|  | Run No. | | | | | |
| --- | --- | --- | --- | --- | --- | --- |
|  | 1 | 2 | 3 | 4 | 5 | 6 |
| Reaction temperature (T° C.) | 380 | 410 | 450 | 380 | 380 | 420 |
| WHSV (V HR − 1) | 40 | 40 | 40 | 60 | 100 | 8 |
| $\left(\frac{4}{V} + 0.10\right) T - \frac{1000}{V} - 40$ | 11 | 17 | 25 | 6.7 | 3.2 | 87 |
| 1.5T − 3V | 450 | 495 | 555 | 390 | 210 | 606 |
| This invention or not | YES | YES | NO | YES | NO | NO |
| Non-aromatic component cracking ratio (%) | | | | | | |
| nonane | 34.8 | 57.4 | 87.6 | 22.8 | 13.1 | 97.8 |
| methyloctanes | 24.5 | 42.5 | 66.4 | 16.0 | 9.0 | 85.4 |
| dimethylheptanes | 16.5 | 28.2 | 43.8 | 10.3 | 5.3 | 68.6 |
| trimethylcyclohexanes | 21.1 | 34.6 | 52.8 | 14.0 | 8.1 | 73.9 |
| Aromatic ring loss (%) | 0.07 | 0.20 | 0.39 | 0.06 | 0.02 | 0.54 |
| Xylene loss (%) | 0.19 | 0.62 | 1.21 | 0.16 | 0.05 | 1.71 |

What we claim is:

1. A process for continuously isomerizing xylene, which comprises subjecting a hydrocarbon feed material comprising a major proportion of a xylene isomer mixture and a minor proportion of non-aromatic hydrocarbons to xylene isomerization reaction, isolating a specific xylene isomer from the resulting isomerization reaction mixture, and recycling the remaining hydrocarbon mixture to the xylene isomerization reaction; wherein the hydrocarbon feed material or the xylene isomerization reaction mixture is treated with hydrogen in the presence of a cracking catalyst comprising (a) a zeolite selected from zeolites ZSM-5, ZSM-11, ZSM-12, ZSM-34 and ZSM-48 series, at least 20% of its cation site being occupied by a cation of a metal selected from alkali metals and alkaline earth metals, and (b) a refractory amorphous inorganic oxide having platinum supported thereon, at a temperature and a weight hourly space velocity which simultaneously satisfy the following inequalities (i) to (iv)

$$300 \leq T \leq 425 \quad \text{(i)}$$

$$5 \leq V \leq 200 \quad \text{(ii)}$$

$$\left(\frac{4}{V} + 0.10\right) T - \frac{1000}{V} - 40 \geq 5 \quad \text{(iii)}$$

$$1.5T - 3V \leq 600 \quad \text{(iv)}$$

wherein T represents the temperature (°C.), and V represents the weight hourly space velocity (hr$^{-1}$), thereby to crack the non-aromatic hydrocarbons in the hydrocarbon feed material or the xylene isomerization reaction mixture.

2. The process of claim 1 wherein the zeolite is of the zeolite ZSM-5 or ZSM-11 series.

3. The process of claim 1 wherein 20 to 95% of the cation site of the zeolite is occupied by a cation of a metal selected from alkali metals and alkaline earth metals.

4. The process of claim 1 wherein said metal is selected from lithium, sodium and strontium.

5. The process of claim 1 wherein the refractory amorphous inorganic oxide is gamma-alumina.

6. The process of claim 1 wherein 0.005 to 5% by weight, based on the weight of the refractory amorphous inorganic oxide, of platinum is supported on the inorganic oxide.

7. The process of claim 1 wherein the weight ratio of the platinum-supported amorphous inorganic oxide to the zeolite in the cracking catalyst is in the range of from 0.05 to 5.

8. The process of claim 1 wherein the hydrocarbon feed material contains 0.05 to 5% by weight, based on the weight of the feed material, of the non-aromatic hydrocarbons.

9. The process of claim 1 wherein the treatment of the hydrocarbon feed material or the xylene isomerization reaction mixture is carried out at a temperature and a weight hourly space velocity which simultaneously satisfy the following inequalities (i) to (iv)

$$320 \leq T \leq 410 \quad \text{(i)}$$

$$10 \leq V \leq 100 \quad \text{(ii)}$$

$$\left(\frac{4}{V} + 0.10\right) T - \frac{1000}{V} - 40 \geq 10 \quad \text{(iii)}$$

$$1.5T - 3V \leq 570 \quad \text{(iv)}$$

wherein T and V are as defined in claim 1.

* * * * *